United States Patent
Lan et al.

(10) Patent No.: US 6,225,049 B1
(45) Date of Patent: May 1, 2001

(54) HUMAN INSULINOMA-ASSOCIATED CDNA

(75) Inventors: Michael S. Lan, Rockville, MD (US); Abner L. Notkins, McLean, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/246,489

(22) Filed: May 19, 1994

Related U.S. Application Data

(63) Continuation of application No. 07/901,715, filed on Jun. 17, 1992, now abandoned.

(51) Int. Cl.$^7$ ............................ C12Q 1/68; G01N 33/53; C12N 15/63; C12N 15/85
(52) U.S. Cl. ............................ 435/6; 435/7.1; 435/320.1; 435/325; 530/350; 530/387.1; 530/388.1; 536/23.5; 536/24.31
(58) Field of Search ............................. 435/6, 7.1, 320.1, 435/325; 536/23.5, 24.31; 530/350, 387.9, 387.1, 388.1, 387, 7; 935/77, 78

(56) References Cited

U.S. PATENT DOCUMENTS

| | | |
|---|---|---|
| 4,783,420 | 11/1988 | DelVillano et al. .................. 436/513 |
| 4,843,019 | 6/1989 | Escribano-Crespo et al. ....... 436/501 |
| 4,959,320 | 9/1990 | Uemura et al. .................. 435/240.27 |
| 4,962,048 | 10/1990 | Kajiji et al. ........................... 436/548 |
| 4,994,565 | 2/1991 | Okamoto ................................. 536/27 |
| 4,996,298 | 2/1991 | Salem et al. .......................... 530/397 |
| 5,173,408 | * 12/1992 | Lange, III et al. ................. 435/91.1 |
| 5,429,921 | * 7/1995 | Harpold et al. ........................... 435/4 |

FOREIGN PATENT DOCUMENTS

| | | |
|---|---|---|
| 394694 | 4/1991 | (JP) . |
| 8904841 | 6/1989 | (WO) . |

OTHER PUBLICATIONS

Kita et al. (1990) Biochem. Biophys. Res. Comm. 166 (1):101–108.*
Guazzi et al. (1990) Embo J. 9(11): 3631–3639.*
Harlowe et al. (1988) Antibodies:A Laboratory Manual, Published in Cold Spring Harbor, p. viii, 53–243, 511–612.*
Alpert, et al. Cell 53: 295–308 (1988).
Birnstiel, et al. Cell 41: 349–359 (1988).
Bordi, et al. Archiv. A Pathol. Anat 413: 387–398 (1988).
Bray, et al. Proc. Natl. Acad. Sci. (USA) 83: 8893–8897 (1986).
Brown, et al. Nature 324: 215 (1986).
Brunstedt, et al. Methods in Diabetes Research 1(C) 245–258 (1985).
Caput, et al. Proc. Acad. Natl. Sci (USA) 83: 1670–1674 (1986).
Chomczynski, et al. Anal. Biochem. 162: 156–159 (1987).
Contreas, et al. Pancreas 5(5): 540–547 (1990).
Emi, et al. Gene 41: 305–310 (1986).
Falkmer, et al. Evolution and Tumor Pathology of the Neuroendocrine System Eds. Elsevier, Amsterdam 433–452 (1984).
Terazone, et al. J. Biol. Chem. 263: 2111–2114 (1988).
Tomita, et al. Biochem. Biophys, Res. Comm. 158: 569–575 (1989).
Wiedenmann, et al. Proc. Natl. Acad. Sci. (USA) 83: 3500–3504 (1986).
Williams, et al. Genes and Development 2: 1557–1569 (1988).
Batra, et al. J. Cell Biol 109(4 Part 2): 195A (1989).
Dear, et al. Cancer Research 48: 5203–5209 (1988).
Haglund, et al. Br. J. Cancer 53: 189–195 (1986).
Haglund, et al. Br. J. Cancer 60: 845–851 (1989).
Iguchi, et al. Horm. Metab. Res. 23: 486–489 (1991).
Makisumi, et al. Gastroenterologia Japonica 25(2): 236–243 (1990).
Martens, Gerard. FEB 234(1): 160–164 (1988).
Patel, et al. J. Clin. Pathol 43: 377–378 (1990).
Takasawa, et al. Diabetes 35: 1178–1180 (1986).
Theodorsson, E. Acta Oncologica 28: 319–324 (1989).
Hara, et al. Nucleic Acids Res. 19(25): 7097–7104 (1991).
Helman, et al. J. Biol. Chem. 263: 11559–11563 (1988).
Huse, et al. Science 246: 1275 (1989).
Kadonaga, et al. Cell 51: 1079–1090 (1987).
Kim, et al. Cancer 66: 2134–2143 (1990).
Kozak, et al. Nucl. Acids Res. 15: 8125–8148 (1987).
Lee, et al. Proc. Natl. Acad. Sci. (USA) 88: 2825–2829 (1991).
Madsen, et al. Endocrinology 113: 2135–2144 (1983).
Maxam, et al. Proc. Natl. Acad. Sci (USA) 74: 560–565 (1977).
Miller, et al. EMBO J. 4: 1609–1614 (1985).
Mitchell, et al. Science 245: 371–378 (1989).
Muller, et al. Nature 336: 544–551 (1988).
Norman, et al. Cell 55: 989–1003 (1988).
Pearson, et al. Proc. Natl. Acad. Sci (USA) 85: 2444–2448 (1988).
Rindi, et al. Virchows Archiv A Pathol Anat 419: 115–129 (1991).
Rosenberg, et al. Nature 319: 336–339 (1986).
Ryseck, et al. Nature 334: 535–537 (1988).
Schwartz, et al. Gastroenterology 85: 1411–1425 (1983).
Schweinfest, et al. Genet. Annal. Techn. Appl. 7: 64–70 (1990).
Shaw, wt al. Cell 46: 659–667 (1986).
Shirasu, et al. Biochem. 104: 259–264 (1988).
Sukhatme, et al. Cell 53: 37–43 (1988).
Teitelman, et al. Devel. Biol. 121: 454–466 1987).

* cited by examiner

*Primary Examiner*—Lisa B. Arthur
(74) *Attorney, Agent, or Firm*—Knobbe, Martens, Olson & Bear, LLP.

(57) ABSTRACT

A novel insulinoma-associated, neuroendocrine tumor-associated cDNA sequence is disclosed. The sequence and fragments thereof are useful for the diagnosis and identification of insulinoma and neuroendocrine tumors. The invention relates to a method for identifying a cancer employing the insulinoma-associated nucleic acid, polypeptide and antibody generated thereto.

23 Claims, 7 Drawing Sheets

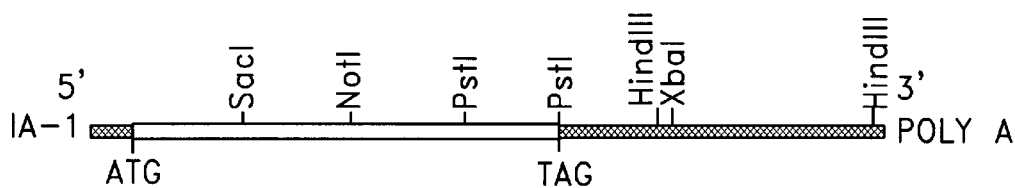
*FIG. 1A*
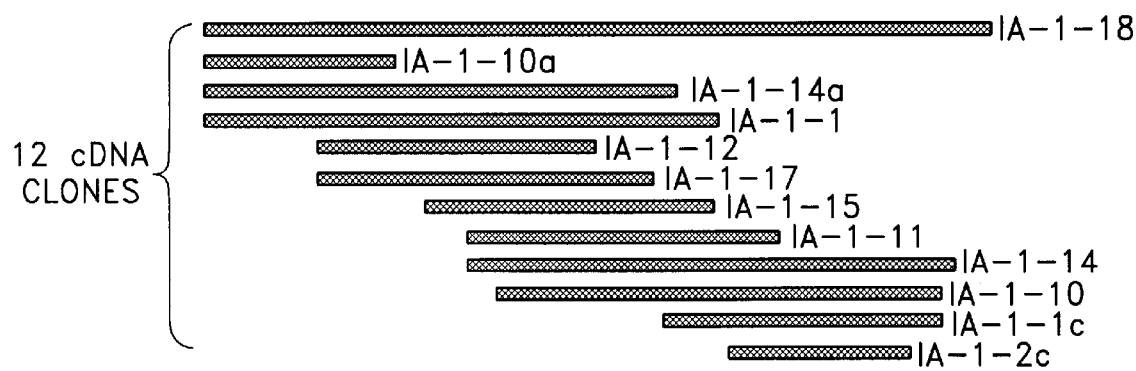
*FIG. 1B*
*FIG. 1C*
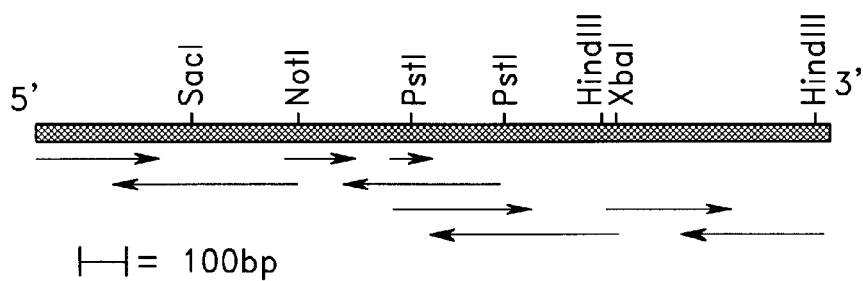
*FIG. 1D*

```
GGGCGCAGAGCTGGGCCGCCGAGCCGTCGCCGGCGCGTCGCCGAGCCGAGTCCCGGCCAGCCCGCCCCCGGGCAATGGGCCGCCGCCACTGAGGCCGGGGCCGAG      100

CGCGGAGGGGCGACCGAGCCAGTGCCGTGCCCTGCGCCCTGCCCGGCCTTCCTGTGAAGCGCAGCAAGAAGTCCACGCCCGTTTCCTA      200
                  ─────────>                                                ─────────>
                      20                                            25                27
                                                M  P  R  G  F  L  V  K  R  S  K  K  S  T  P  V  S  Y   18

CCGGGTCCGCGGGGCGGAGGACGGCGACCGCGCACTGCTGCTCTCGCCCAGCTGCGGGGGGCGCGAGCCCCGAGCCCGCCGAGCCCCGGTCCCCGGG      300
                      <─────────
                        22
R  V  R  G  G  E  D  G  D  R  A  L  L  L  S  P  S  C  G  G  A  R  A  E  P  P  A  P  S  P  V  P  G    51

CCGCTGCCGCCGCCGCCGCCGGAGCGCGCCCATGCAGGAGCGCTGCCGCCGCCGCGCTTGCCTGCCCAGCCCCAGCCCGGGCCCCAGGGCCCGGG      400
                                ─────────>
                                 23
P  L  P  P  P  P  P  A  E  R  A  H  A  A  A  L  A  A  A  L  A  C  A  P  G  P  Q  P  P  P  Q  G  P  R  A    85

CCGCGCACTTCGGCAACCCGAGGCTGCGCACCCCGAGTCCCGCTCTACAGTCCCCACCGGCGCCCGTGAGCCGCGAGCACAGAAGCACAGTACTTCGAACG      500
                                                                              <─────────
                                                                                  21
                                                                                              26

A  H  F  G  N  P  E  A  A  H  P  A  P  L  Y  S  P  T  R  P  V  S  R  E  H  E  K  H  K  Y  F  E  R    118

CAGCTTCAACCTGGGCTCGCCGGTCTCGGCCGAGTCCTTCCCCACGCCCGCGCTGCTCGGAGAGGGCGGCGGCGGGGCGAGCTGGCGGA      600
                                                    ─────────>
                                                       19

S  F  N  L  G  S  P  V  S  A  E  S  F  P  T  P  A  A  L  L  G  G  G  G  G  A  S  G  A  G  G    151

GGGCGGCACCTGCCGCGGCGGCGACCCGCTGCTCTTCGCGCCGGCGGAGCTCAAGATGGGCACGGCGTTCTCGGCTGCCGAGGCGGCCGCCCGGGCC      700
                                                <─────────
                                                    13

G  G  T  C  G  G  D  P  L  L  F  A  P  A  E  L  K  M  G  T  A  F  S  A  G  A  E  A  A  A  R  G  P  P    185

CCGGCCCCCCACTGCCCCCCTGCCGCGCCCCTGCGGCCCCAGCGGCGGAGAAAGCGGCCCCGCCAAGGCAGTCAAGGCCCC      800
```

FIG.2A

```
G  P  P  L  P  P  A  A  A  L  R  P  P  G  K  R  P  P  P  T  A  A  E  P  P  A  A  K  A  V  K  A  P              218
GGGGCCAAGAAGCCAAGCCATCCGCAAGCTGCACTTCGAGGACGAGTGACCACGTGCCCGTGCTGGGGCTCAAGATCAAGGAGGCCCGGTGGAG                900
         16
         ────>
      ────────
         18
G  A  K  K  P  K  A  I  R  K  L  H  F  E  D  E  V  T  T  S  P  V  L  G  L  K  I  K  E  G  P  V  E             251
GCGCCGGCGGCCGCGCGGGGCGCGGCCCGCTGGGCGAGTTCATCTGCCAGCTGTGCAAGGAGTACGCCGACCCGTTCGCGCTGGCCAGC                     1000
                                      ────────>
                                         17
A  P  R  G  R  A  G  C  A  A  R  P  L  G  E  F  I  C  Q  L  C  K  E  E  Y  A  D  P  F  A  L  A  Q  H          285
ACAAATGCTCGCGCATCGTGCGTGTGGAGTACCGCTGTCCCGAGTGCGCCAAGGTCTTCAGCTGCCCGCCAACCTGGCCTCGCACCGCCTGGCACAA             1100
       ────────>
          15
      <────────
         14
K  C  S  R  I  V  R  V  E  Y  R  C  P  E  C  A  K  V  F  S  C  P  A  N  L  A  S  H  R  R  W  H  K             318
ACCGGCGGCCCGCGCCCCGCGCCCCGCGAGCCAGAAGCAGCAGCCAGGGCTGAGGCGGCGGAGGCACCGGCGGCAGCGACCGGACACG                      1200
                              <────────
                                 12
P  R  P  A  P  A  A  A  R  A  P  E  P  E  A  A  A  R  E  A  P  G  G  G  S  D  R  D  T                         351
CCGAGCCCCGGCGCGTGTCCGATGCGGGCTCGGAGAGCGGCTCTACGAGTGCCATCACTGCGCCAAGAAGTTCCGCCGCCAGGCCTACCTACGCAAGC            1300
                                                                                   <────────
                                                                                       11
P  S  P  G  G  V  S  E  S  G  S  E  D  G  L  Y  E  C  H  H  C  A  K  K  F  R  R  Q  A  Y  L  R  K  H          385
ACCTGCTGGCCGACCACCAGGCGCTGCAGGCCAAGGGCGCGCCCCCGCCTAGCGCCGAGGACCTACTGGCCTTGTACCCGGGCCCTGACGAGAAGGC             1400
<─────
A  L  L  A  H  H  Q  A  L  Q  A  K  G  A  P  L  A  P  P  A  E  D  L  L  A  L  Y  P  G  P  D  E  K  A          418
                                                                            ─────
                                                                              6
```

*FIG. 2B*

```
GCCCCAGGAGGCGCCGGCGACGGCGAGGGCCGCGGCCGTGCTGGGCCTGAGTGCTCCGCCCAGTGCCACCTGCCCCAGTGTGCGGAGAGTCGTTCGCC          1500
 P   A   E   A   A   G   D   G   E   G   A   G   V   L   G   L   S   A   S   A   E   C   H   L   C   P   V   C   G   E   S   F   A           451
                                                         ───────────→
                                                             3
AGCAAGGGCGCTCAGGAGCGCCACTCGCTGCTGCACGCGCCAGGTGTTCCCCTGCAAGTACTGCCCGGCCACCTTCTACAGCTCGCCGGCCTTA          1600
 S   K   G   A   Q   E   R   H   L   R   L   L   H   A   A   Q   V   F   P   C   K   Y   C   P   A   T   F   Y   S   S   P   G   L   T           485
                                       ←───────────
                                            7
CGCGGCACATCAACAAGTGCCACCCATCCGAAAACAGACAGGTGATCCTCCTGCAGGTGCCCGTGCCCCGGCCTCCACCCCGGC                          1700
 R   H   I   N   K   C   H   P   S   E   N   R   Q   V   I   L   L   Q   V   P   V   R   P   A   C   END
                                                                                              ───────
CCCGAACTGTGCCTTCGCTTGGAGACCCACAAAGAGAGTCGCGCCTGCACGCCCGAGTCCGGCTGGGGAGCCTCGCCCCCCACCG                         1800
 ───────────→
      4
GGTGAGAGTCGTCTCCGCTTCTCCGGTGTGGCGTGACGGTAACCCCATACTCCTCTTTTGAACCCCACTTTTACGTTTGTGTCCCT                       1900
CCGCCTCCCCATGGCGCAACAGAGTCAGTCTCTTTCTGTACAAGGGAGAAAAAGCTGTACGGCGTTGTCTGTGGTTGTCTCGTGGAAGCCTCCCCTTGGCGGGGA  2000
GAAGCTTTTTTTCTGCTAGTATCGCTGTGTTCATGGTCTGTGTCTAGAAATGCGGTCTGGTCTCGCCTACCAATCTCTGCTCTGTCTTCTCTATGTATGTAGCGTTA 2100
                                                                                    ───────────→
                                                                                         8
CGGGTTGTTTTGGGTGAATCTTGAGGAATAAATGCCTTTAGCCTGTAAATTGAACTTCCCACACGATTAGCTTTATTATGGCTTGTGAACT                  2200
GCTGGAGTCTGGCTTTTACCTTTTGTATGTGAACAATCAAATGCTTAAAAAAAGAGTTTTCTTTTAGTATAGCCACAAATGCCTGAACTGTTGTCTTGGG        2400
                                                         ─────
TAGGACTATCAGTTCCCCTAAATGTATATGTATGTTGATTTATGAGTAATTGTTATTTATTATTATTATGAAGATTATGATATATTT                      2500
                                          *****      *********
GATTGCAGATTTTTTGCGCGCCCTGCCCCCTCCCACCCTGCCACTCTTGACATTCCACTGTGCGTTTAGAAGAGAGCCTTTTCTAAAGGGATCTGCT           2600
                                    *****
TAAAGTTTAACTTTTATACCTATCTGAGTGAATTACAGACAACCTATCATTTATTCTGCTTCGAGGGTCCCCAGGGCCCTTGTACAACCGACAGCTCTT         2700
                                              *****
ACTTTTAAATGCAATCTCTTTCTACATACATTATTTCTTAATGTTAGCTATTATTATGAAAAGCTTCAATAGAACTGTTTCAACTGTATAACTATTTAC         2800
                                                                                             *****
TATTCAAATAAATATTTTCAAAGTCAAAAAAAAAAAAA                                                                       2838
```

*FIG. 2C*

```
  1  MPRGFIVKRS  KKSTPVSYRV  RGGEDGDRAL  LLSPSCGGAR
 51  GPLPPPPPAE  RAHAALAAAL  ACAPGPQPPP  QGPRAAHFGN
101  SPTRPVSREH  EKHKYFERSF  NLGSPVSAES  FPTPAALLGG
151  GGGTCGGDRL  LFCAPAELKMG TAFSAGAEAA  RGPGPGPPLP
201  RPPPPTAAEP  KKPKAIRKLH                FEDEVTTSPV
      *
251  EAPRGRAGA   ARPLG
266  EFICQLCKEE  YADPFALAQH  KCSRIVRV
294  EYRCPECAKV  FSCPANLASH  RRWHKPR
321  PAPAAARAPE  PEAAARAEAR  EAPGGGSDRD  TPSPGGVSES
366  LYECHHCAKK  FRRQAYLRKH  LLAHHQAL
394  QAKGAPLAPP  AEDLLALYPG  PDEKAPQEAA  GDGEGAGVLG
440  CHLCPVCGES  FASKGAQERH  LRLLHAAQ
468  VFPCKYCPAT  FYSSPGLTRH  INKCHPSE
496  NRQVILLQVP  VRPAC
```

AEPPAPSPVP
PEAAHPAPLY
GGGGASGAG
PAAALRPPGK
****
LGLKIKEGPV

GSEDG

LSASAE

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
        (A) LENGTH: 2838 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: IA-1

(xi) SEQUENCE DESCRIPTION: SEQ ID NO:1:

```
GGGCGCAGAG CTGGGCCGAG CCGTCGCCGG CGCCACGCGA GTCCCGCAGC CGCCGCGCCC      60

GGGCAATGGG CCGGGGGCAC TGAGGGCCGC CGGGGCCGAG CGCGGAGGGG GGACCGAGCC     120

AGTGCCGTGC CCTCGGGCCG CGCCAACATG CCCCGCGGCT TCCTGGTGAA GCGCAGCAAG     180

AAGTCCACGC CCGTTTCCTA CCGGGTCCGC GGCGGCGAGG ACGGCGACCG CGCACTGCTG     240

CTCTCGCCCA GCTGCGGGGG CGCCCGCGCC GAGCCCCCGG CGCCGAGCCC GGTCCCCGGG     300

CCGCTGCCGC CGCCGCCGCC CGCGGAGCGC GCCCATGCAG CGCTCGCCGC CGCGCTTGCC     360

TGCGCGCCTG GGCCGCAGCC ACCCCCGCAG GGCCCGCGGG CCGCGCACTT CGGCAACCCC     420

GAGGCTGCGC ACCCCGCGCC GCTCTACAGT CCCACGCGGC CCGTGAGCCG CGAGCACGAG     480

AAGCACAAGT ACTTCGAACG CAGCTTCAAC CTGGGCTCGC CGGTCTCGGC CGAGTCCTTC     540

CCCACGCCCG CCGCGCTGCT CGGAGGGGGC GGCGGCGGCG GCGCGAGCGG AGCTGGCGGA     600

GGCGGCACCT GCGGCGGCGA CCCGCTGCTC TTCGCGCCCG CCGAGCTCAA GATGGGCACG     660

GCGTTCTCGG CTGGCGCCGA GGCGGCCCGC GGCCGGGCC CCGCCCCCC ACTGCCCCCT     720

GCCGCCGCCC TGCGGCCCCC GGGAAAGCGG CCCCCGCCCC CTACCGCCGC GGAGCCGCCC     780

GCCAAGGCAG TCAAGGCCCC GGGCGCCAAG AAGCCCAAGG CCATCCGCAA GCTGCACTTC     840

GAGGACGAGG TGACCACGTC GCCCGTGCTG GGGCTCAAGA TCAAGGAGGG CCCGGTGGAG     900

GCGCCGCGGG GCCGCGCGGG GGGCGCGGCG CGGCCGCTGG GCGAGTTCAT CTGCCAGCTG     960

TGCAAGGAGG AGTACGCCGA CCCGTTCGCG CTGGCGCAGC ACAAATGCTC GCGCATCGTG    1020
```

-continued

```
CGTGTGGAGT ACCGCTGTCC CGAGTGCGCC AAGGTCTTCA GCTGCCCGGC CAACCTGGCC    1080

TCGCACCGCC GCTGGCACAA ACCGCGGCCC GCGCCCGCCG CCGCCCGCGC GCCGGAGCCA    1140

GAAGCAGCAG CCAGGGCTGA GGCGCGGGAG GCACCCGGCG GCGGCAGCGA CCGGGACACG    1200

CCGAGCCCCG GCGGCGTGTC CGAGTCGGGC TCCGAGGACG GGCTCTACGA GTGCCATCAC    1260

TGCGCCAAGA AGTTCCGCCG CCAGGCCTAC CTACGCAAGC ACCTGCTGGC GCACCACCAG    1320

GCGCTGCAGG CCAAGGGCGC GCCGCTAGCG CCCCCGGCCG AGGACCTACT GGCCTTGTAC    1380

CCCGGGCCCG ACGAGAAGGC GCCCCAGGAG GCGGCCGGCG ACGGCGAGGG GGCCGGCGTG    1440

CTGGGCCTGA GTGCGTCCGC CGAGTGCCAC CTGTGCCCAG TGTGCGGAGA GTCGTTCGCC    1500

AGCAAGGGCG CTCAGGAGCG CCACCTGCGC CTGCTGCACG CCGCCCAGGT GTTCCCCTGC    1560

AAGTACTGCC CGGCCACCTT CTACAGCTCG CCCGGCCTTA CGCGGCACAT CAACAAGTGC    1620

CACCCATCCG AAAACAGACA GGTGATCCTC CTGCAGGTGC CCGTGCGCCC GGCCTGCTAG    1680

AGCGCGCCCT CCACCCCGGC CCCCGAACTG TGCCTTCGCT TGGAGACCCA CAAAGAGAGT    1740

GCGCCCTGCA CGCCCCGAAC CCGAGTCCGC GCTGGGGGAG CCTCGCCCCC GCCCCCACCG    1800

GGTGAGAGTG TCGTCTCCGC TTCTCTCGGT GTGGCGTGAC GGTAACCCCA TACTCTCCTT    1860

TTGACTCCTT TTGGAACCCC CACTTTTACG TTGTGTCCCT CCGCCTCCCC CATGGCGCAA    1920

CAGGAGTCAG TCTCTTTCTG TACAAGGGAG AAAAGCTGTA CGCGTTTGTC TCGTGGTTGG    1980

AAGCCTCCCC TTGGCGGGGA GAAGCTTTTT TTCTTGCTAG TATTCGCTGT GTTCATGGTC    2040

TAGAAATGCG GTCTGGTCTC GCCTCGCCTA CCAATCTCTG CTCTCTATGT ATGTAGCGTA    2100

CGGGTTGTTT TGGGTGAATC TTGAGGAATA AATGCCTTTA TATTTCACAG GCTGTAAATT    2160

GAACTTCCCA CACGATTAGC TTTATTATGG CTTGTGAACT GCTGGAGTCT GGCTTTACCT    2220

TTTTGTATGT GAACAAATCA AATTGCTTAA AAAAGAGTTT TCTTTAGTAT AGCCACAAAT    2280

GCCTTGAACT GTTGTCTGGG ATTGTTTTGT GGGGGAGGG AAGGGAGTGT TCCGAAGATG    2340

CTGTAGTAAC TGCCTCAGTG TTTCACGTAA GACTTTTTGG TTTGATCATC TTTGTTGAGG    2400

TAGGACTATC AGTTCCCTCT AAATGTATAT GTTGATTTAT GAGTAATTGT TATTTATTCT    2460

TTATTTATTT ATATTAATTA TGAAGATTAT GATATTATTT GATTGCAGAT TTTTTTGGCG    2520

CGCTGCCCCC TCCCCACCCT GCCACTCTTG ACATTCCACT GTGCGTTTTA GAAGAGAGCC    2580

TTTTTCTAAA GGGATCTGCT TAAAGTTTTA ACTTTTATAC CTATCTGAGT GAATTACAGA    2640

CAACCTATCA TTTATTCTGC TTCGAGGGTC CCCAGGGCCC TTGTACAACC GACAGCTCTT    2700

ACTTTTAAAT GCAATCTCTT TTCTACATAC ATTATTTTCT TAATTGTTAG CTATTTATAG    2760

AAAGCTTCAA TAGAACTGTT TCAACTGTAT AACTATTTAC TATTCAAATA AAATATTTTC    2820

AAAGTCAAAA AAAAAAAA                                                   2838
```

(2) INFORMATION FOR SEQ ID NO:2:

(i) SEQUENCE CHARACTERISTICS:
        (A) LENGTH: 510 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:2:

```
Met Pro Arg Gly Phe Leu Val Lys Arg Ser Lys Lys Ser Thr Pro Val
1               5                   10                  15

Ser Tyr Arg Val Arg Gly Gly Glu Asp Gly Asp Arg Ala Leu Leu Leu
                20                  25                  30

Ser Pro Ser Cys Gly Gly Ala Arg Ala Glu Pro Pro Ala Pro Ser Pro
            35                  40                  45

Val Pro Gly Pro Leu Pro Pro Pro Pro Ala Glu Arg Ala His Ala
    50                  55                  60

Ala Leu Ala Ala Ala Leu Ala Cys Ala Pro Gly Pro Gln Pro Pro Pro
65                  70                  75                  80

Gln Gly Pro Arg Ala Ala His Phe Gly Asn Pro Glu Ala Ala His Pro
                85                  90                  95

Ala Pro Leu Tyr Ser Pro Thr Arg Pro Val Ser Arg Glu His Glu Lys
                100                 105                 110

His Lys Tyr Phe Glu Arg Ser Phe Asn Leu Gly Ser Pro Val Ser Ala
            115                 120                 125

Glu Ser Phe Pro Thr Pro Ala Ala Leu Leu Gly Gly Gly Gly Gly Gly
130                 135                 140

Gly Ala Ser Gly Ala Gly Gly Gly Thr Cys Gly Gly Asp Pro Leu
145                 150                 155                 160

Leu Phe Ala Pro Ala Glu Leu Lys Met Gly Thr Ala Phe Ser Ala Gly
                165                 170                 175

Ala Glu Ala Ala Arg Gly Pro Gly Pro Gly Pro Leu Pro Pro Ala
                180                 185                 190

Ala Ala Leu Arg Pro Pro Gly Lys Arg Pro Pro Pro Thr Ala Ala
                195                 200                 205

Glu Pro Pro Ala Lys Ala Val Lys Ala Pro Gly Ala Lys Lys Pro Lys
210                 215                 220

Ala Ile Arg Lys Leu His Phe Glu Asp Glu Val Thr Thr Ser Pro Val
225                 230                 235                 240

Leu Gly Leu Lys Ile Lys Glu Gly Pro Val Glu Ala Pro Arg Gly Arg
                245                 250                 255

Ala Gly Gly Ala Ala Arg Pro Leu Gly Glu Phe Ile Cys Gln Leu Cys
                260                 265                 270

Lys Glu Glu Tyr Ala Asp Pro Phe Ala Leu Ala Gln His Lys Cys Ser
                275                 280                 285

Arg Ile Val Arg Val Glu Tyr Arg Cys Pro Glu Cys Ala Lys Val Phe
290                 295                 300

Ser Cys Pro Ala Asn Leu Ala Ser His Arg Arg Trp His Lys Pro Arg
305                 310                 315                 320

Pro Ala Pro Ala Ala Arg Ala Pro Glu Pro Glu Ala Ala Ala Arg
                325                 330                 335

Ala Glu Ala Arg Glu Ala Pro Gly Gly Ser Asp Arg Asp Thr Pro
                340                 345                 350

Ser Pro Gly Gly Val Ser Glu Ser Gly Ser Glu Asp Gly Leu Tyr Glu
                355                 360                 365

Cys His His Cys Ala Lys Lys Phe Arg Arg Gln Ala Tyr Leu Arg Lys
                370                 375                 380

His Leu Leu Ala His His Gln Ala Leu Gln Ala Lys Gly Ala Pro Leu
385                 390                 395                 400

Ala Pro Pro Ala Glu Asp Leu Leu Ala Leu Tyr Pro Gly Pro Asp Glu
                405                 410                 415
```

```
Lys Ala Pro Gln Glu Ala Ala Gly Asp Gly Glu Gly Ala Gly Val Leu
            420                 425                 430
Gly Leu Ser Ala Ser Ala Glu Cys His Leu Cys Pro Val Cys Gly Glu
        435                 440                 445
Ser Phe Ala Ser Lys Gly Ala Gln Glu Arg His Leu Arg Leu Leu His
    450                 455                 460
Ala Ala Gln Val Phe Pro Cys Lys Tyr Cys Pro Ala Thr Phe Tyr Ser
465                 470                 475                 480
Ser Pro Gly Leu Thr Arg His Ile Asn Lys Cys His Pro Ser Glu Asn
                485                 490                 495
Arg Gln Val Ile Leu Leu Gln Val Pro Val Arg Pro Ala Cys
            500                 505                 510
```

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

GTTCCCCTGC AAGTACT                                                17

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

GTGCCTTCGC TTGGAGACCC A                                     21

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GCAATTTGAT TTGTTCA                                                17

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

AACGACTCTC CGCACACTG                                            19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

ACCTGCAGGA GGATCACCT                                            19

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

CCACACGATT AGCTTTA                                              17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

ACGCCACACC GAGAGAA                                              17

(2) INFORMATION FOR SEQ ID NO:10:

(i) SEQUENCE CHARACTERISTICS:
        (A) LENGTH: 17 base pairs
        (B) TYPE: nucleic acid (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

TTCACTCAGA TAGGTAT                                              17

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TGCTTGCGTA GGTAGGCCT                                            19

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

AGGACGGGCT CTACGAGT                                             18

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

TCAAGATGGG CACGGCGTTC T                                         21

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
        (ii) MOLECULE TYPE: DNA (genomic)

(iii) HYPOTHETICAL: NO (iv) ANTI-SENSE: NO (xi) SEQUENCE DESCRIPTION: SEQ ID NO:14:

TACTCCACAC GCACGATG                                                    18

(2) INFORMATION FOR SEQ ID NO:15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

ATCGTGCGTG TGGAGTAC                                                    18

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

CAAGAAGCCC AAGGCCAT                                                    18

(2) INFORMATION FOR SEQ ID NO:17:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

AGTTCATCTG CCAGCTG                                                     17

(2) INFORMATION FOR SEQ ID NO:18:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO:18:

ATGGCCTTGG GCTTCTT                                                                17

(2) INFORMATION FOR SEQ ID NO:19:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

CGTGCCCATC TTGAGCT                                                                17

(2) INFORMATION FOR SEQ ID NO:20:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

GCCACGCGAG TCCCGCA                                                                17

(2) INFORMATION FOR SEQ ID NO:21:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

ACTTGTGCTT CTCGTGC                                                                17

(2) INFORMATION FOR SEQ ID NO:22:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

CCGCGCACTG CTGCTCT                                                        17

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

GCGGCGAGCG CTGCATG                                                        17

(2) INFORMATION FOR SEQ ID NO:24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

ACGGCACTGG CTCGGTC                                                        17

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

CTGCGCTTCA CCAGGAA                                                        17

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

AGGTTGAAGC TGCGTTCGAA GTACT                                               25

(2) INFORMATION FOR SEQ ID NO:27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

AGGAAACGGG CGTGGACTTC TTGCTGCCCA GGAA    34

HUMAN INSULINOMA-ASSOCIATED CDNA

This application is a continuation of application Ser. No. 07/901,715, filed Jun. 17, 1992 which is now abandoned.

FIELD OF THE INVENTION

The present invention relates to the field of cancer diagnosis and therapy. In particular, this invention relates to the isolation and use of a novel insulinoma-associated neuroendocrine tumor-associated cDNA, polypeptide and antibody generated thereto for research and diagnostic purposes.

BACKGROUND OF THE INVENTION

The pancreas contains cells of both the exocrine and endocrine system. Endocrine cells are found scattered throughout the pancreas in clusters of cells termed the islets of Langerhans, or pancreatic islets. Histological staining and analysis reveal several cell types within the islets. Two of the most prevalent cells are the alpha cells which constitute approximately 20 percent of the islet cells, and the beta cells which constitute about 75 percent of the islet cells. Other cells types within the islet include the delta cell and the pancreatic polypeptide cell.

While beta cells comprise the major cell type present in the pancreatic islets, beta cells are less than 2% of the total pancreatic mass. Beta cells are the only cell type in the body that secrete insulin hormone to regulate glucose metabolism. These cells and other endocrine cell types of the pancreatic islets release their hormones directly into the circulation.

Endocrine cells of the pancreas share similarities with neuroendocrine tissue including cells of the pituitary gland, thyroid medulla, parathyroid, carotid body, adrenal medulla and small cells of the lung. It is generally accepted that pancreatic islet cells express a number of neuroectodermal markers. These markers include neuronal-specific enolase synaptophysin, and tyrosine hydroxylase (Polak et al., 1984 In *Evolution and Tumor Pathology of the Neuroendocrine System*. S. Falkmer et al., Eds. Elsevier, Amsterdam, p. 433; Weidenmann et al., *Proc. Natl. Acad. Sci., USA* 83:3500–3504 (1986); and Teitelman et al., *Devel. Biol.* 121:454–466 (1987) respectively). Dissociated pancreatic islet cells can extend neurite-like processes in vitro and these processes contain neurofilament protein (Teitelman, *Devel. Biol.* 142:368–379, 1990).

The incidence of pancreatic cancer in industrialized countries has increased over the past twenty years. The majority of pancreatic cancers have morphologic characteristics of cells of the exocrine pancreas, however some pancreatic cancers are derived from beta cells and alpha cells. These tumors are referred to as insulinomas and glucagonomas respectively. Like their nontransformed counterparts, insulinomas and glucagonomas share similarities with neuroendocrine tumors. Examples of other neuroendocrine tumors include small cell lung carcinoma, pituitary tumors, thyroid medullary carcinoma and pheochromocytoma. These cells also express common neuroendocrine markers such as those described in the preceding paragraph (Alpert et al., *Cell* 53:295–308, (1988) and Rindi et al., *Virchow Archiv A Pathol Anat* 419:115–129 (1991)).

Definitive identification of a tumor type, survival statistics and therapeutic strategies for treating a tumor are all dependant to some extent on the ability of the physician to differentiate one tumor type from another. Polyclonal or monoclonal antibodies as well as nucleic acid probes can be used to screen biopsy specimens to determine the derivation of a particular tumor. Effective pancreatic and neuroendocrine cancer treatment depends on the early diagnosis and identification of tumor tissue. Antibodies generated from antigen obtained from purified pancreas cell populations or antibodies directed to known polypeptides present in pancreatic cells can be used to differentiate one pancreatic tumor from another.

U.S. Pat. No. 4,962,048 to Kajiji et al. identified hybridoma cell lines producing monoclonal antibodies reactive with human pancreatic cancer cells. The antibodies cross-reacted with several types of pancreatic cancer cells and were strongly reactive with a variety of tumors derived from a number of different organs. The antibodies failed to react uniquely with one identifiable cancer or related group of cancers. None of the antibodies reacted well with neuroendocrine-related tumors.

Antibodies directed to known polypeptides can be used to screen neuroendocrine-related tumors. Immunohistochemical staining with several different antibodies can be used to differentiate pancreatic, endocrine and neuroendocrine tumors (Bordi et al., *Archiv A Pathol. Anat.* 413:387–398, 1988). However, the differentiation of tumor tissue using a panel of antibodies is labor intensive. Multiple antibodies are separately reacted with duplicate cell cultures or tissue sections to generate a pattern of antibody reactivity that can be compared to a control panel characteristic of a particular tumor type to determine the origin of a particular tumor (Kim et al., *Cancer* 66:2134–2143, 1990). The results from these panels can be ambiguous since antibody staining is often diffuse or nonspecific. The intensity of positive signals may vary between matched samples making positive tissue identification difficult.

Antibodies generated from tumor cell lysates can also be used to identify a particular tumor type. However, antibodies generated from cell lysates are directed toward many different polypeptides. Some of the antibodies may be cell specific, but a great number of the antibodies will be directed toward common cellular antigens. Once antibodies are generated to cell lysates, intensive study is required to confirm the uniqueness of a particular antigen and to determine the usefulness of the antibody as a diagnostic or therapeutic. Thus, identifying cell specific antibody, obtained through immunization with a particular tumor cell lysate is not a particularly efficient way to identify unique cellular antigen.

No nucleic acid probes are currently available to uniquely identify neuroendocrine tumor tissue. The identification of transcripts unique to an isolated tumor type or related group of tumors would be useful for nucleic acid based assays. The presence of a common transcript or protein among related tumor cells suggests the presence of a common regulatory mechanism and potentially a common therapy.

Subtractive hybridization is a useful tool for identifying uniquely expressed mRNA within a given cell type. Subtractive hybridization permits cDNA clones to be identified that represent mRNA expressed in one cell population and absent in a second cell population without prior knowledge of the gene or the gene product. This method has been used in other systems to identify candidate tumor suppressor genes and proteins unique to colon carcinoma and hepatic cancer (Lee et al., *Proc. Natl. Acad. Sci., USA* 88:2825–2829, 1991 and Schweinfest et al., *Genet Annal. Techn. Appl.* 7:64–70, 1990).

As outlined above, the identification of polypeptide unique to a particular cancer cell is important for developing diagnostic tests and therapeutic strategies. There is a need for diagnostic tools that permit the correct identification of human insulinomas and neuroendocrine tumors.

SUMMARY OF THE INVENTION

The present invention relates to a recombinant polynucleotide having a sequence comprising at least 10 sequential nucleotides or complementary nucleotides from the sequence identified as SEQ ID NO:1. In a preferred embodiment of this invention, this recombinant polynucleotide is contained in a vector. In one aspect of this preferred embodiment, the vector directs the expression of the recombinant polynucleotide sequence. The recombinant polynucleotide is preferably RNA or DNA.

The invention also relates to cells containing the polynucleotide vector and to the translation products encoded therefrom. Isolated polypeptide comprising at least 6 sequential amino acids as disclosed in SEQ ID NO:2 are also contemplated within the scope of this invention. In another preferred embodiment of this invention, monoclonal antibody or polyclonal antibody that specifically bind to SEQ ID NO:2 are prepared and isolated.

In another preferred embodiment of the invention, a method is disclosed for identifying a cancer in a vertebrate comprising obtaining a biological sample containing nucleic acid from the vertebrate, denaturing any double-stranded nucleic acid present in the sample, adding polynucleotide having a sequence corresponding to SEQ ID NO:1 or a sequential fragment thereof and detecting polynucleotide hybridizing to the sample, wherein the detection of hybridization indicates the presence of cancer. In one aspect of this invention, the polynucleotide fragment is at least 10 nucleotides in length and in another, the preferred fragment is at least 18 nucleotides in length. In another aspect of this invention, the sample is a tissue section. The polynucleotide is preferably labelled for detection and the detecting step preferably includes measuring the amount of label in the sample.

In yet another preferred embodiment of this invention, a method is provided for identifying a cancer in a vertebrate comprising obtaining a cell sample from the vertebrate, adding antibody recognizing the polypeptide corresponding to SEQ ID NO:2 and detecting antibody binding to the sample, wherein the detection of antibody binding indicates the presence of cancer. The method is preferably formatted as an enzyme-linked immunosorbant assay and in another preferred embodiment the method employs a Western Blot assay format.

BRIEF DESCRIPTION OF THE FIGURES

FIGS. 1A, 1B, 1C, and 1D provides the restriction map and sequencing strategy for IA-1. FIG. 1A is a restriction map of the full-length IA-1 sequence. The open box illustrates the position of the open reading frame. FIG. 1B illustrates the relative position of IA-1-34 relative to the full length IA-1 transcript. FIG. 1C identifies the relative positions of twelve additional clones isolated from a random-primed human λZAPII insulinoma library using IA-1-34 as a probe. IA-1-10a and IA-1-12 were selected using IA-1-18 as a probe. The IA-1-18 clone contains sequence from base pair positions 4 through 2819. FIG. 1D illustrates the sequencing strategy of IA-1. Lengths and orientations of the sequenced regions are indicated by the arrows.

FIGS. 2A–2C provide the cDNA sequence and deduced amino acid sequence for human insulinoma-associated antigen, IA-1, corresponding to SEQ ID NO:1. The underlined initiation codon corresponding to the first labelled methionine residue is designated as position 1 for the amino acid sequence. The amino acid sequence is provided as ID SEQ NO:2. The stop at position 510 identifies the termination codon TAG. Start codons, stop codons, and polyadenylation signals are underlined. ATTTA rich sequences are identified by asterisk. The numbered arrows provide the positions of sequencing primers SEQ ID NO:3 through SEQ ID NO:27.

FIG. 3 highlights chemically distinct features of the amino and carboxyl domains of IA-1. The protein sequence can be divided into two domains: the amino-terminal domain (1-250 a.a.) and carboxyl-terminal domain (251-510 a.a.). The dibasic amino acids are underlined in the amino-terminal domain and a putative amidation signal sequence is identified by asterisk. The carboxyl-terminal domain is symmetrically arranged to highlight the position of the zinc-finger motif. The consensus residues of the zinc-finger motifs are highlighted in bold lettering.

FIG. 4 identifies the consensus sequences of the zinc-finger motif associated with IA-1 as compared with consensus regions from known zinc-finger containing proteins. Amino acid sequences of human IA-1, murine Egr-1, Drosophila Kruppel, human Sp1 and Zenopus TFIIIA (finger 2) are compared as illustrated. The conserved residues (Cys, His, Phe and Leu) of zinc-finger motifs are boxed in.

FIG. 5A illustrates the results obtained from a Northern blot containing total RNA from insulinoma tissues as compared with other transformed cells lines. Human insulinoma tissues and small cell lung carcinoma cells were positive for IA-1 RNA. FIG. 5B is a Northern blot containing murine insulinoma and glucagonoma cell lines.

DETAILED DESCRIPTION OF THE INVENTION

Figure 5A:
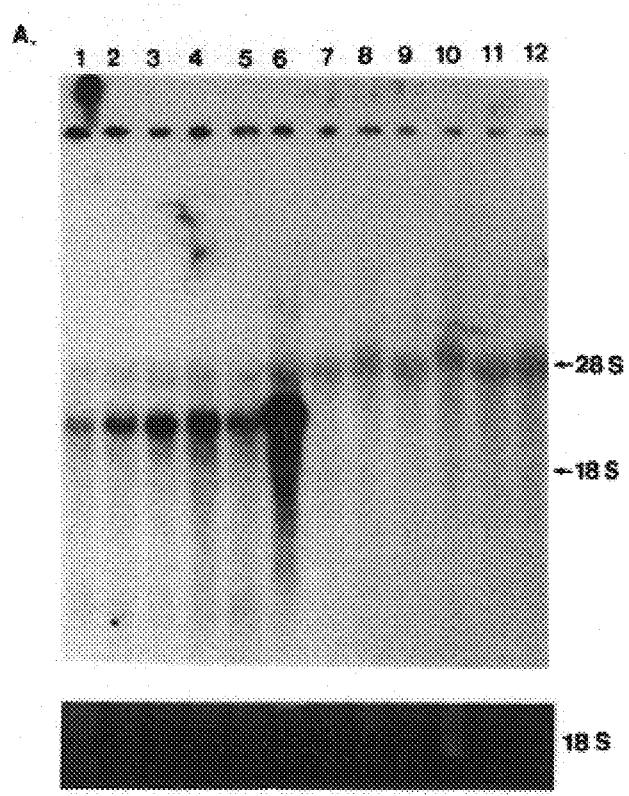
FIGS. 5A and 5B contains photographs of autoradiograms from Northern blot analyses of total cellular RNA separated on 1% agarose/formaldehyde gels.

The term recombinant polynucleotide is used herein to denote polynucleotide (RNA or DNA) produced through recombinant methods well known in the art of molecular biology.

The term complementary nucleotides are those nucleotides that form base pairs with the parent nucleotide sequence. This term is also well recognized in the art.

Sequential nucleotides are those nucleotides positioned in succession within a sequence.

The term polypeptide is used broadly to include peptide, polypeptide and protein.

A nucleic acid vector is a linear or circular, RNA or DNA molecule that facilitates nucleic acid manipulation or transfer. Nucleic acid vectors are well known in the art of molecular biology.

The full-length sequence of a novel cDNA clone termed insulinoma-associated antigen (IA-1) is disclosed here as SEQ ID NO: 1. The sequence of the corresponding translation product is provided as SEQ ID NO:2. The IA-1 gene is uniquely expressed in malignant neuroendocrine tissues and/or cell lines. Its sequence includes zinc-finger DNA-binding motifs and dibasic amino acid pro-hormone conversion sites. The restricted tissue distribution and unique sequence motifs of IA-1 suggest that IA-1 may function as a regulatory factor in islet cell transformation.

IDENTIFICATION OF UNIQUE INSULINOMA PROTEIN

The preparation of subtraction libraries requires the selection of one or more cell types in addition to the principle cell type of interest. Thus to obtain unique sequences from human insulinoma cells, cDNA from an insulinoma cell library was hybridized with cDNA from a human glucagonoma cell library to remove homologous sequences. The choice of cell line determines the population of unique sequences remaining after subtractive hybridization. Glucagonoma cells were chosen in this particular example because the cells are both neuroendocrine in origin and because their nontransformed counterpart resides proximate to beta cells in the pancreatic islets.

Subtractive hybridization identified a novel transcript expressed in insulinoma cells. The subtraction library (ISL-53) was constructed using human insulinoma (beta cell tumor) and glucagonoma (alpha cell tumor) cDNA phagemid libraries. The novel cDNA clone, IA-1, was identified by differential screening. The full-length sequence (2838 bp) of the cDNA clone was determined by double-strand sequencing of 13 cDNA clones isolated from both the human insulinoma subtraction library and another insulinoma random-primed library.

Library Construction

Human insulinoma and glucagonoma tissue samples were obtained from the National Cancer Institute, NIH (Bethesda, Md.). Tissue type was confirmed by immunoperoxidase staining for insulin, glucagon, somatostatin, gastrin and/or pancreatic polypeptide using techniques well known in the art. Antibodies to insulin, glucagon, somatostatin, gastrin and pancreatic polypeptide are available from a number of manufacturers. For current source availability of these antibodies see the Linscott Directory of Immunological & Biological Reagents (Mill Valley, Calif.).

There are a variety of methods known in the art for obtaining cDNA libraries. Phagemid cDNA libraries were prepared from glucagonoma and insulinoma cell RNA. Total RNA was isolated from human insulinoma and glucagonoma tissues (NCI, NIH) using an acid guanidinium thiocyanate phenol/chloroform extraction method (Chomczynski, P. et al. *Anal. Biochem.* 162:156–159, 1987 which is hereby incorporated by reference). Poly(A)⁺ RNA was purified by passing the sample twice through oligo-dT cellulose columns. Phagemid cDNA libraries were constructed using Invitrogen's Librarian II system (San Diego, Calif.) following manufacturer's instructions. Aliquots of Poly(A)⁺ RNA were primed with oligo-dT (Invitrogen, San Diego, Calif.). Double-stranded linker-ligated cDNAs generated from the Librarian II system greater than 750 bp were selected from agarose gels for further study. The cDNA was electroeluted and ligated with pcDNAII (Invitrogen) and transformed into competent *E. coli* cells and amplified on LB plates using ampicillin. Poly(A)⁺ RNA from human insulinoma was also random-primed (see Example 5) using a cDNA human insulinoma library (RP-IL) in a λZAPII phage vector system (Stratagene, La Jolla, Calif.).

Subtraction libraries can be generated using commercially available kits such as those obtained from Invitrogen (San Diego, Calif.). Similarly, libraries may be prepared using methods known to those with skill in the art such as those described by Schweinfest et al. (supra.) or Hara et al. (*Nucl. Acids Res.,* 19:7097–7104, 1991). As one example of a method for generating an insulinoma-specific subtraction library, R408 helper phage (Invitrogen) was used to infect insulinoma and glucagonoma libraries to generate single-stranded phagemid DNA. Phage produced from these infections were harvested and the single-strand DNA was extracted from the phage and purified using techniques well known to those with skill in the art and detailed in the Invitrogen subtraction library kit instructions.

Glucagonoma phagemid single-strand DNA was photobiotinylated using photobiotin acetate. Single-stranded phagemid DNA derived from the insulinoma library was coprecipitated with an excess of photobiotinylated glucagonoma single-strand phagemid DNA. The DNA was resuspended, denatured and cooled to permit hybridization. Following hybridization, streptavidin was used to separate out both single-strand glucagonoma DNA and glucagonoma DNA bound to insulinoma DNA. The remaining single-strand DNA was converted to double strand DNA using methods known in the art and the reaction mixture was used to transform competent *E. coli* (see Example 2). Other subtractive hybridization methods that could similarly be used, include, but are not limited to, methods employing oligonucleotide labelled beads and avidin-agarose extraction techniques. Transformed colonies were selectively plated onto agar and colonies were picked and stored for future analysis.

Screening of the Subtraction Library

Plasmid DNA was initially isolated from individual cDNA clones obtained from the insulinoma-glucagonoma subtraction library (ISL-153) and screened against probes derived from insulinoma, glucagonoma and HeLa cells. Clones reacting with insulinoma probes, but not glucagonoma and HeLa cell probes were selected for further study. Example 3 provides an exemplary initial screening technique. Plasmid DNA was isolated using the alkaline lysis mini-preparation technique, well known in the art. The purified DNA was digested with HindIII and XhoI restriction endonucleases and separated by agarose gel electrophoresis. The DNA was transferred to Nytran paper (Schleicher & Schuell, Keene, N.H.) and replica blots were screened separately using $^{32}$P-end-labeled mRNA isolated from insulinoma, glucagonoma and HeLa cells.

Homology to GenBank Database Sequences

The selected clones were partially sequenced for approximately 200 bp from both ends of the vector using reverse and forward primers that bind to λ ZAP II DNA (United States Biochemical, Cleveland, Ohio). These sequences were compared with sequences available in the GenBank DNA database. Three of the cDNA clones revealed sequence similarity (>95%) with trypsin (Emi, et al. *Gene* 41:305–310, 1986), chymotrypsin (Tomita, et al., *Biochem. Biophys. Res. Comm.* 158: 569–575, 1989) and pancreatic protease E (Shirasu, et al. *J. Biochem.* 104: 259–264, 1988) and may be derived from contaminating acinar tissue associated with the original insulinoma. A fourth clone showed similarity (>99%) with the islet regenerating protein (reg) previously described by Terazono, et al. *J. Biol. Chem.* 263:2111–2114 (1988). A fifth clone had a high sequence similarity (>99%) with a GTP-binding protein (alpha subunit) (Bray, et al., *Proc. Natl. Acad. Sci. USA* 83: 8893–8897, 1986) and a sixth clone had high homology (>97%) to pancreastatin hormone precursor-chromogranin A (Helman, et al., *J. Biol. Chem.* 263: 11559–11563, 1988). The seventh clone, IA-1-34 (see FIG. 1), and the eighth clone, IA-2, had no identifiable sequence homology with sequences in the GenBank database. Northern analysis, using each of the first six clones as probes revealed message size consistent with that previously reported for each of these proteins as described in Example 4. The seventh clone, IA-1, and the eighth clone, IA-2, based on sequence comparison, proved to be novel. Northern analysis revealed mRNAs of 3.0 Kb and 3.8 Kb, respectively. Transcript size and homologies are summarized in Table I.

When the predicted 510 amino acid sequence of IA-1 (see FIGS. 2A–2C) was matched to protein sequences in the database, IA-1 had a 20 to 30% homology with members of the zinc-finger protein family. The similarity of the protein sequence was limited to the consensus sequences within the zinc-finger motif. No similarities were found in the flanking regions.

TABLE I

Isolation and identification of cDNA clones from a human substraction library

| cDNA clone | Message Size* | Identification# |
|---|---|---|
| 1 | 0.8 kb | Trypsin |
| 2 | 1.1 kb | Chymotrypsin |
| 3 | 0.9 kb | Elastase |
| 4 | 0.8 kb | Regenerating protein (reg) |
| 5 | 2.5 kb | GTP-binding protein (alpha subunit) |
| 6 | 2.2 kb | Chromogranin A |
| 7 | 3.0 kb | IA-1 |
| 8 | 4.0 kb | IA-2 |

*Message size of each clone was estimated from Northern analyses.
Each clone was partial sequenced approximately 200 bps from both ends of pcDNAII vector by using reverse and forward primers and the sequence was matched to the GenBank database (Pearson et al., Proc. Natl. Acad. Sci. USA 85:244–2448, 1988).

Generating the Full-Length cDNA Clone of IA-1

The initial clone, IA-1-34, isolated from the subtraction library (ISL-153) contained a 1508 bp sequence upstream from the poly(A) tail (FIG. 1B). To further analyze full length IA-1, a random-primed λZAPII cDNA library (Stratagene) from human insulinoma tissues was constructed (RP-IL). IA-1-34 insert DNA was used as a probe to screen the insulinoma λZAPII library (RP-IL). Additional positive clones with insert sizes ranging from 0.6 to 2.8 kb were isolated (see Example 5 and FIG. 1C). The longest clone, IA-1-18, extending from 4 to 2819 bp, was used as a probe for later tissue distribution studies (Example 6). Ten cDNA clones isolated from the secondary screening of the random-primed library contained regions overlapping with the IA-1-34 insert. Two addition clones were isolated using IA-1-18 as a probe. cDNA clones of various lengths were subjected to double-strand sequencing using internal primers that primed from both ends of the insert. These primers are provided as SEQ ID NOS: 3–27 and their positions are illustrated in FIG. 2. The sequencing strategy is illustrated in FIG. 1D and detailed in Example 5.

The full-length cDNA sequence and the deduced protein sequence are shown in FIGS. 2A–2C. The cDNA sequence corresponds to an mRNA containing a 147 bp 5'-untranslated region and an 1150 bp 3'-untranslated region containing two polyadenylation consensus sequences, AATAAA, located at positions 2127 and 2807. The proposed significance of the AATAAA sequences is described by Birnstiel, et al., Cell 41: 349–359 (1985). The first ATG, in nucleic acid position 66, is followed by a termination codon, TGA, in position 81. The next ATG codon at position 147 contains a long open reading frame of 1530 nucleotides and is flanked by sequences that fulfill the Kozak translation consensus sequence, GCCA/GCC[ATG]G (Kozak, M. Nucl. Acids Res. 15: 8125–8248, 1987). There are also seven ATTTA sequences positioned between the two polyadenylation signals.

Structural Features of the Deduced Amino Acid Sequence

Certain predictions can be made from the nucleic acid and protein sequence of the IA-1 clone. While these predictions are not absolute, they are based on consensus data obtained from other protein sequence/function studies and help those with skill in the art to further characterize IA-1 polypeptide.

The large open reading frame of IA-1 indicates that the protein contains 510 amino acids and has a deduced pI value of 9.1 and an unmodified molecular mass of 52,923 daltons.

The amino acid sequence can be divided into two domains based upon distinct chemical features associated with each domain (FIG. 3). The N-terminal domain (1-250 a.a.) has a high content of proline (18%), glycine (12.8%), and alanine (16%). The proline-enriched (20 to 30%) domain of DNA-binding proteins has been found in many mammalian transcription factors, including enhancer-binding protein, AP-2 (Williams, T. et al. Genes and Development 2:1557–1569, 1988), Jun (Ryseck et al., Nature 334:535–537, 1988), lymphocyte-specific factor, OCT-2 (Muller, M. M. et al. Nature 336: 544–551, 1988), and serum response factor, SRF (Norman, C. et al. Cell 55:989–1003, 1988) and represents one type of activation domain (Mitchell, P. J. et al. Science 245: 371–378, 1989).

In addition to a proline rich domain, there are four classical pro-hormone dibasic conversion sites at positions 8-9, 11-12, 221-222, and 227-228 with an amidation signal sequence, Pro-Gly-Lys-Arg, at position 198-201 (Kreil, G. (1986) Protein Compartmentalization, pp. 61–70 Springer-Verlag, Inc., New York.). Peptide hormone precursors of insulin, glucagon, pancreatic polypeptide and somatostatin contain dibasic amino acid cleavage sites that are associated with protein processing. In the nervous and endocrine system many bioactive peptides possess a C-terminal α-amide group. The α-amide moiety is generated from enzyme cleavage at the amidation signal sequence with the conversion of peptides with the structure —X-Gly into the form —X-NH1$_2$. The presence of the α-amide group was shown to be important for pancreatic polypeptide (Schwartz, T. W. Gastroenterology 85: 1411–1425, 1983) as well as other amidated peptides. (Tatemoto, K. et al. J. Biol. Chem. 263:2111–2114, 1978). The presence of potential dibasic pro-hormone processing sites and the amidation signal sequence in the putative activation domain demonstrated that IA-1 is a novel cDNA clone without similarities to other DNA-binding proteins.

Figure 4:
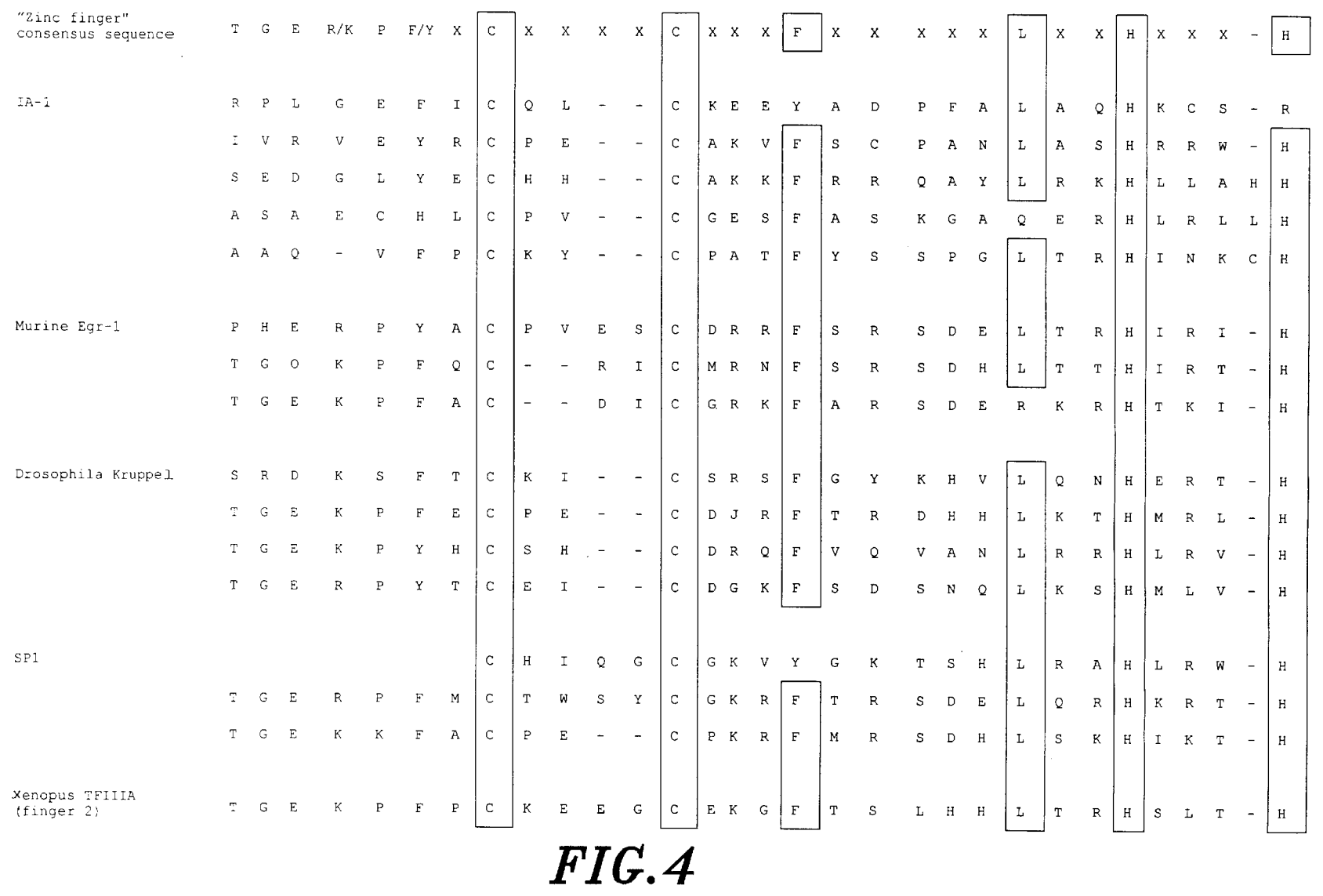

The C-terminal domain (251-510 a.a.) contains five putative "zinc-finger" DNA-binding motifs of the form $X_3$-Cys-$X_{2-4}$-Cys-$X_{12}$-His-X3-4-His-$X_4$, described as a consensus sequence for members of the Cys$_2$-His$_2$ class (Mitchell et al., supra.). FIG. 3 illustrates a zinc-finger motif in the middle of the carboxyl-domain of IA-1 located between two tandem repeated zinc-finger motifs spaced 45/46 amino acids from each side. The first zinc-finger sequence, positioned at amino acids 266-293, lacks the last histidine residue at position 289. A comparison of IA-1 zinc-finger motifs with the consensus sequence of various zinc-finger DNA-binding proteins is shown in FIG. 4 (Kadonaga, J. T. et al. Cell 51:1079–1090 (1987); Sukhatme, V. P. et al. Cell 53:37–43 (1988); Brown, R. S. et al. Nature 324:215 (1986); Rosenberg, U. B., et al. Nature 319:336–339 (1986)).

The conserved residues, Cys, His, Phe and Leu, are identical to other known proteins containing zinc-finger domains. However, the residues positioned between each zinc-finger motif are different from published sequences. Zinc-finger motifs were first discovered by Miller, J. et al. (EMBO J. 4:1609–1614, 1985) in Zenopus transcription factor IIIA. Subsequently, other proteins with zinc-finger domains were shown to be involved in DNA-binding and in many aspects of eukaryotic gene regulation, such as differentiation and growth signals, proto-oncogenes and transcription factors. The IA-1 cDNA clone contains five zinc-finger motifs and a proline-rich activation domain which resembles other DNA-binding proteins and may be responsible for recognizing and binding IA-1 to DNA. The organization of the zinc-finger motifs and activation domains are unique.

The nucleotide sequence contains an 1150 bp 3'-untranslated region with seven ATTTA sequences located between two polyadenylation signals, AATAAA. The presence of pro-hormone and amidation sequences in the amino-terminal domain strongly suggests that the ATTTA sequence element may serve as a recognition signal for the specific degradation of mRNA as reported for proto-oncogenes and inflammatory mediators such as lymphokines and cytokines (Shaw, G. et al. *Cell* 46: 659–667, 1986 and Caput, et al., *Proc. Natl. Acad. Sci. USA* 83:1670–1674, 1986).

Tissue Expression of IA-1 Gene

Fragments of IA-1 were used as probes to determine the tissue specificity of IA-1 gene expression. RNA isolated from five human insulinomas and a variety of other human, mouse and rat cell lines were separated by 1% agarose formaldehyde gel electrophoresis. The RNA was capillary-transferred to Nytran paper and probed with the cDNA clone IA-1-18 corresponding to cDNA nucleotide positions 4 through 2819 (Table II and FIG. 5).

Normal human tissues were obtained from the National Disease Research Interchange (NDRI, Philadelphia, Pa.). Cell lines, HPAF-2 (pancreatic adenocarcinoma), BT-20 (breast carcinoma), SKMEL (melanoma), DM-6 (melanoma), and HeLa (ovarian carcinoma) were obtained from Dr. R. S. Metzgar (Duke University, N.C.); JAR (choriocarcinoma), BeWo (choriocarcinoma), SK-N-SH and SK-N-MC (neuroblastoma), NCI-H69 (small cell lung carcinoma), U-78-MG (glioblastoma), SW579 (thyroid carcinoma), AtT-20/D16v-F2 (mouse pituitary tumor), PC-12 (rat pheochromocytoma), GH-3 (rat pituitary tumor), 6-23, clone 6 (rat medullary thyroid carcinoma), Y-1 (mouse adrenal cortex tumor), and F-9 (mouse embryonal carcinoma) were obtained from the American Type Culture Collection (Rockville, Md.). α-TC1 (mouse glucagonoma) and β-TC1 (mouse insulinoma) were kindly provided by Dr. E. H. Leiter (Bar Harbor, Me.). Tumor cell lines were cultured in modified Eagle's medium supplemented with 10% fetal calf serum in 5% $CO_2$ at 37° C. or according to supplier's instructions.

Mouse islets were isolated from Balb/c pancreas as described by Brunstedt, J. et al., *Methods in Diabetes Research* 1(*C*): 245–258 (1985) which is hereby incorporated by reference. Pancreases from twenty mice were digested with collagenase P (Boehringer Mannheim Biochemicals, Indianapolis, Ind.) and islets were isolated by Percoll gradient (Pharmacia, Uppsala, Sweden) separation. The enriched islets were then extracted for total RNA using methods described in Example 1.

Five of five human insulinomas and a small cell lung carcinoma (NCI-H69) expressed IA-1 as a 3.0 kb message (FIG. 5A). A summary of the tissue expression work is provided in Table II. Normal tissues express little of this gene. Normal human pancreas, testes, lymph node, brain, lung, liver, stomach, spleen, thyroid, pituitary, kidney, colon were negative by Northern analysis. RNA preparations from enriched normal murine islet cells that contained concentrated quantities of beta cell RNA had a significant increase in insulin-specific message as compared to total pancreas RNA. However, these beta cell enriched RNA preparations were still negative for IA-1.

IA-1 was present in several neuroendocrine tumors including pheochromocytoma, medullary thyroid carcinoma, insulinoma, pituitary tumor and small cell lung carcinoma. The cDNA probe also recognized a 3.0 kb message from insulinoma cell lines of mouse (β-TC1), rat (RIN), and hamster (HIT). The message was detected in cell lines from mouse pituitary tumor (AtT-20/D16v-F2), rat pheochromocytoma (PC-12), rat pituitary tumor (GH-3) and rat medullary thyroid carcinoma (6-23) (Table II). Other cell lines such as mouse adrenal cortex tumor (Y-1); mouse embryonal carcinoma (F-9), mouse NIH-3T3 and rat testicular tumor (LC-540) were negative on Northern analysis. The restricted tissue distribution for IA-1 indicated that it recognized a protein specifically expressed by human insulinoma tissues, murine insulinoma cell lines, and other neuroendocrine tumors.

| | | IA-1 EXPRESSION IN HUMAN, MOUSE, AND RAT TUMORS[a] | | |
|---|---|---|---|---|
| | | Human | Mouse | Rat |
| Positive | | Insulinoma tissue[b] | Pituitary tumor AtT-20/D1 6v-F-2 | Pheochromocytoma adrenal medullary, PC-12 |
| | | Small cell lung carcinoma NCI-H69 | Insulinoma β-TC-1 | Pituitary tumor GH-3 Insulinoma RIN |
| | | | Glucagonoma α-TC-1[c] | |
| | | | | Medullary thyroid carcinoma 6-23 |
| Negative | | Choriocarcinoma JAR BeWo | Adrenal tumor (Cortex) Y-1 Embryonal carcinoma F-9 | Testicular tumor Leydig cell, LC-540 |
| | | Neuroblastoma SK-N-SH SK-N-MC Giloblastoma U-87-MG | Fibroblast NIH-3T3 | |

IA-1 EXPRESSION IN HUMAN, MOUSE, AND RAT TUMORS[a] -continued

| Human | Mouse | Rat |
|---|---|---|
| Thyroid carcinoma | | |
| SW-579 | | |
| Breast carcinoma | | |
| BT-20 | | |
| Pancreatic carcinoma | | |
| HPAF-2 | | |
| Ovarian carcinoma | | |
| HeLa | | |
| Melanoma | | |
| SKMEL | | |
| DM-6 | | |

[a]This is a summary table from northern analysis data
[b]Five human insulinoma tissues were tested
[c]Very weak signal was detected with a longer exposure

Use of IA-1 as a Tumor Marker

IA-1 gene sequences or fragments of the IA-1 gene sequence are useful for identifying and verifying the origin of tumors. The cloned fragments of IA-1 illustrated in FIG. 1C, full length IA-1 or fragments thereof can be labelled with radioactive isotopes, biotin, fluorescent tags or the like to generate markers for the identification of insulinomas or other tumors of neuroendocrine origin.

In a study to explore the diagnostic application of IA-1, the IA-1-34 insert was labelled and used as a probe to perform Northern analyses (see Example 7). RNA was isolated from biopsies of human small cell lung carcinomas. IA-1 mRNA was present in 22 of 22 human small cell lung carcinoma cell lines and 8 of 8 human small cell lung cancer biopsies. No IA-1 mRNA was identified in 15 of 15 non-small cell lung carcinomas. The unique tissue distribution of this gene for transformed neuroendocrine tissue makes it an ideal candidate for both a nucleic acid and protein tumor marker in clinical, diagnostic and research applications.

It is further contemplated within the scope of this invention that nucleic acid fragments, polypeptide and polypeptide fragments encoded therefrom, or antibody reactive with polypeptide or polypeptide fragments can be used as part of a panel of tumor markers. Diagnostic research related kits and assays employing recombinant gene fragments as probes are well known in the art. It is anticipated that IA-1 cDNA, RNA generated therefrom and DNA or RNA fragments of IA-1 can be readily adapted for assay formats for diagnostic or research purposes. Assay formats employing nucleic acid probes include but are not limited to in-situ hybridization of biopsy and tissue sections, Polymerase chain reaction (PCR) related assays, Dot-blot manifold assays or the like. These assays can provide a rapid and reproducible means for identifying pancreas or neuroendocrine tumors. Thus recombinant nucleic acid sequences corresponding to IA-1 or sequential nucleotide fragments thereof can be used to positively identify a particular tumor.

A method for identifying the presence of neuroendocrine related cancer from a patient involves obtaining a sample from a patient that contains nucleic acid. The sample may be a purified nucleic acid, cell lysate, a tissue section, a blood sample or the like. Double-stranded nucleic acid or double stranded regions of a single-stranded nucleic acid are preferably denatured by heat, sodium hydroxide or other methods known to these with skill in the art. Following denaturation, polynucleotide of at least 10 nucleotides or more preferably at least 18 nucleotides in length, corresponding or complementary to SEQ ID NO: 1 is added to the sample under conditions that promote hybridization (see Example 4 and Davis et al. (1986) *Basic Methods in Molecular Biology*. Elsevier Press). Unique fragments of SEQ ID NO:1 of at least 10 nucleotides in length, preferably at least 15, 18, or 20 nucleotides in length, are contemplated within the scope of this invention.

Polypeptide fragments generated from the amino acid sequence provided in FIG. 2 and in SEQ ID NO:2, polypeptide generated by recombinant expression vectors containing IA-1, or in vitro translated polypeptide can be used to generate antibody reactive with IA-1 protein both in vitro and in vivo. These polypeptide fragments are preferably unique fragments at least 6, 10, or 15 amino acids in length. Methods for generating polypeptide or protein fragments by chemical synthesis, recombinant vector expression or in vitro translation are well known in the art and would not require undue experimentation. Once peptide or polypeptide fragments are obtained, the protein may be used to immunize animals for the generation of polyclonal and monoclonal antibody in accordance with standard techniques. Example 8 provides one example of a method for the preparation of monoclonal antibody reactive with IA-1 protein. Other methods for generating monoclonal antibodies and for genetically modifying these antibodies are well known in the art. It is additionally contemplated within the scope of this invention that antibody directed to IA-1 could also be obtained using the polymerase chain reaction to obtain variable antibody domain sequences to then generate a library of antigen combining sites such as the recombinatorial phage libraries described by Huse et al., *Science* 246:1275 (1989).

Monoclonal or polyclonal antibody generated to recombinant protein or peptide fragments of IA-1 using techniques well known to those with skill in the art are used to screen tissue samples by either Western Blot assay, immunostaining of cell lines or tumor tissues, ELISA or the like. Exemplary cell lines that may be used to facilitate antibody screening are provided in Table II. Testing over a range of cell types is used to ensure the cell specificity of the antibody. Antibody reactive with IA-1 can then be employed in any number of antibody related assays. Antibody-related assays are well known in the art and include, but are not limited to Western Blot assays, ELISA format assays, immunohistochemical assays and competitive protein assays such as radio-immuno assays or the like. These formats may be useful as research assays for assessing the functional characteristics of IA-1 and as diagnostic assays for rapid multi-sample analysis.

A general method contemplated within the scope of this invention for identifying a cancer in a vertebrate includes obtaining a cell sample from the vertebrate as a biopsy, tissue section or the like. The sample may be fresh, fixed or frozen and there are methods well known in the art that apply antibody to samples treated in a variety of fixatives. It is further contemplated that samples may be processed in NP40, SDS, other suitable detergents or homogenized to disrupt cell integrity. Antibody specifically binding to the polypeptide corresponding to SEQ ID NO: 2 is added according to procedures and methods compatible with immunohistochemical staining techniques or antibody-utilizing assays such as ELISA's or Western blot assays.

It is also contemplated that antibody or nucleic acid sequences as described herein can additionally be used to rule out a particular type of cancer. Thus these methods are useful for generally identifying cancer in a vertebrate.

It is further contemplated that antibody directed to IA-1 can be used to substantially purify or separate IA-1 from surrounding native protein. Techniques known in the art such as affinity-chromatography or other chromatographic methods that do not employ antibody could be used to isolated native IA-1.

With respect to the DNA and RNA sequences and fragments of the present invention, and also with respect to the proteins and peptides, these materials may advantageously be provided in a non-naturally occurring form. Thus, they may be substantially purified, i.e., they have a degree of purity significantly greater than the naturally occurring form. For example, concentrations of these materials of at least 0.01 $\mu$g/g, preferably at least 0.1 $\mu$g/g, and more preferably 1 or 10 $\mu$g/g typically satisfy this definition. Alternatively, the materials may be provided in an isolated form; that is, they are substantially isolated from or enriched in comparison to the proteins, peptides, or polynucleotides with which they are associated in the natural state. Materials that are, for example, 100, 1000, or 10,000 times more concentrated than in the natural state are considered to be both isolated and purified for purposes of the present invention.

Particular embodiments of the invention will be discussed in detail. These embodiments are intended to illustrate and not limit the scope of the invention.

EXAMPLE I

Library Construction

To construct the phagemid cDNA libraries, total RNA was isolated from human insulinoma and glucagonoma tissues by acid guanidinium thiocyanate phenol/chloroform extraction method (Chomoczynski et al., supra.). Poly(A)$^+$ RNA was purified by twice passing the RNA aliquots through oligo-dT cellulose columns. Phagemid cDNA libraries were constructed using Invitrogen's Librarian II system (San Diego, Calif.). Poly(A)$^+$ RNA (10 $\mu$g) was primed with oligo-dT and the double-stranded linker-ligated cDNAs were size-selected over 750 bp. The sized, electroeluted cDNAs for each library were ligated to 1.5 $\mu$g of prepared PCDNAII. The vector-ligated cDNA was then transformed into 4.0 ml of high efficiency competent MC1061/P3 $E.$ $coli$ cells (Invitrogen, San Diego, Calif.) and amplified on LB agar plates containing ampicillin (50 $\mu$g/ml). The titers of the original libraries were 1.0×10$^6$ colonies for the insulinoma library and 1.5×10$^6$ colonies for the glucagonoma library.

EXAMPLE 2

Subtraction Library

The subtraction cDNA library was constructed using a kit supplied by Invitrogen (San Diego, Calif.). R408 helper phage was used to infect the insulinoma and glucagonoma libraries to generate single-stranded phagemid DNA. An aliquot (1 ml., equivalent to approx. 10$^{10}$ colonies/ml.) of the amplified cDNA library was diluted with 20 ml of LB medium containing ampicillin (50 $\mu$g/ml). Each diluted library was incubated with shaking for one hour at 37° C. Each culture was inoculated separately with 1×10$^6$ pfu of R408 helper phage. After infection, each culture was incubated for an additional 30 minutes, then diluted into 100 ml of LB medium containing ampicillin (50 $\mu$g/ml) and incubated overnight at 37° C. with shaking. The cell pellet was discarded and 10 $\mu$l of 10 mg/ml of RNase A was added to this supernatant (33 ml) along with 5 ml of 8M ammonium acetate and 5 ml of 40% Polyethylene glycol (wt/wt) on ice for three hours. Single-strand DNA was extracted from each library three times with phenol/chloroform and examined on a neutral agarose gel. Photo-biotinylation of the glucagonoma phagemid single-strand DNA was performed according to the manufacturer's procedure (Invitrogen). Single-strand glucagonoma phagemid DNA (20 $\mu$g) was added to 30 $\mu$g of photobiotin acetate in a 1.5 ml screw cap tube, on ice, 10 cm below a sunlamp (General electric #RSM, 275W). The tube was heated for 15 minutes, followed by three to four extractions of the solution with water-saturated 2-butanol.

Subtractive hybridization was performed using ten times molar excess of photobiotinylated glucagonoma single-strand phagemid DNA to remove all sequences present in the insulinoma phagemid DNA library that were substantially homologous with the glucagonoma library. Biotinylated DNA was co-precipitated in ethanol with non-biotinylated DNA, and dissolved in 10 $\mu$l of 2× hybridization buffer (kit supplied). The hybridized mixture was heated to 100° C. for one minute and cooled to 68° C. for 16 to 20 hours. After hybridization the mixture was placed in a 55° C. water bath for five minutes, then diluted with 30 $\mu$l of 10 mM Hepes/EDTA buffer. 10 $\mu$l of 1 mg/ml streptavidin was added followed by extraction with phenol/chloroform. The final subtracted single-strand DNA was converted to double-strand DNA using T7 primer and reverse transcriptase. Aliquots of the reaction mixture were used to transform 100 $\mu$l of competent $E.$ $coli$ cells (DH1$\alpha$F'). Cells were plated onto LB agar plates containing 50 $\mu$g/ml ampicillin. The individual colonies were picked and stored in 96-well microtiter plates at −80° C.

EXAMPLE 3

Screening the Subtraction Library

Mini-preparations of plasmid DNA (triplicates) from the individual insulinoma-glucagonoma subtraction library cDNA clones were prepared using the Plasmid Kit (Qiagen, Chatsworth, Calif.). Purified DNA was digested with HindIII and XhoI restriction endonucleases (BRL, Bethesda, Md.). Digested DNA was separated by 1% agarose gel electrophoresis and transferred to Nytran paper (Schleicher & Schuell, Keene, N.H.) for Southern blot analysis using techniques well known in the art (Davis et al., 1986. $Basic$ $Methods$ $in$ $Molecular$ $Biology$. Elsevier Press). Triplicate blots were pre-hybridized at 50° C. with 40% formamide, 5× SSC, 10 $\mu$g/ml sheared salmon sperm DNA, 6× Denhardt's solution and hybridized with an equal specificity of end-labeled mRNA probe (10$^6$ cpm/ml).

The mRNA probes from insulinoma, glucagonoma and HeLa cells were prepared as follows: 3 $\mu$g of mRNA were dissolved in 10 $\mu$l of a solution containing 0.05 M sodium bicarbonate, pH 9.2, and heated to 85° C. for five minutes.

The reaction mixtures were neutralized with 10 μl of 1.0 M Tris, pH 7.5, and precipitated with 20 μl of 4 M ammonium acetate and 80 μl of ethanol. The partially degraded mRNA was end labelled using T4 polynucleotide kinase (Pharmacia, Piscataway, N.J.) as described by Maxam, A. et al. *Proc. Natl. Acad. Sci. USA* 74: 560–564 (1977), hereby incorporated by reference.

EXAMPLE 4

Northern Analysis of Unique Clones

Northern analysis was performed using total RNA purified by the acid guanidinium thiocyanate method. RNA (20 μg) was fractionated by 1% agarose/formaldehyde gel electrophoresis and transferred to Nytran via capillary blotting (Davis et al., *Basic Methods in Molecular Biology*. (1986) Elsevier Press. pp.143–146). Probe hybridization of Northern blots was performed at 50° C. for 18 hours with 40% formamide, 5× SSC, 10 μg/ml sheared salmon sperm DNA, 6× Denhardt's solution, and $10^6$ cpm/ml labeled probe. The cDNA insert was removed from vector pcDNAII with the appropriate restriction enzymes, Hind III and XhoI (Stratagene, La Jolla, Calif.), separated by agarose gel electrophoresis and purified from the agarose using the Geneclean II kit (Bio 101, Boulder, Colo.). Purified insert (200 ng) was labeled with $^{32}$P-dCTP (Amersham Corp, Arlington Heights, Ill.), using a commercially available random-primed labeling kit (BRL, Bethesda, Md.) and purified by passing the sample over a NICK-column (Pharmacia Piscataway, N.J.).

EXAMPLE 5

IA-I Gene Sequence

IA-1-34 was used as a probe to screen 500,000 plaques obtained from a random-primed λZAPII cDNA library (RP-IL) derived from human insulinoma tissue. Human insulinoma RNA was isolated as described in Example 1. cDNA derived from poly(A)$^+$ RNA was prepared according to kit directions for λZAPII library construction (Stratagene). The library yielded approximately 1.2×10$^6$ pfu/ml. Following kit instructions, the clones from the λZAPII library (RP-IL) that hybridized to IA-1-34 were converted into pBluescript SK$^-$ using helper phage for DNA sequencing. Plasmid DNA obtained from the clones was used for double-strand DNA sequencing using Sequenase T4 DNA polymerase under conditions recommended by the supplier (U.S. Biochemical Corp., Cleveland, Ohio). Internal sense and antisense strand primers were synthesized by Bio-synthesis, Inc. (Denton, Tex.) and are diagrammed in FIGS. 2A–2C and listed as SEQ ID NOS: 3–27. The full-length cDNA nucleotide sequence of IA-1 was obtained by sequencing the 13 independent overlapping clones isolated from the subtraction library and the random-primed λZAPII library. DNA sequences were analyzed using a Model VAX 750 (Digital Electronics Corporation computer) and the GCG Sequence Analysis software package (Devereux, J. et al. *Nucleic Acids Res.* 12: 387–393, 1984, hereby incorporated by reference). The current FASTA database was used for searching both nucleic acid and protein sequence similarities (Pearson, W. R. et al. *Proc. Natl. Acad. Sci. USA* 85: 2444–2448, 1988 hereby incorporated by reference).

EXAMPLE 6

IA-1 Gene Expression in Tissue

Figure 5B:
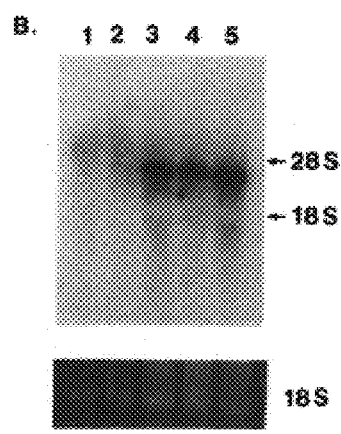

RNA was isolated from five human insulinomas and a variety of other human, mouse and rat cell lines as described supra. using techniques described in Example 1. Total RNA was separated by 1% agarose formaldehyde gel electrophoresis using techniques described in Example 4. Total RNA (20 μg) was isolated from five human insulinoma tissues and loaded onto an agarose formaldehyde gel (FIG. 5A, lanes 1–5). Equal amounts of RNA obtained from the following human cell lines were also loaded onto the gel: small cell lung carcinoma: NCI-H69 (lane 6); neuroblastoma: SK-N-SH (Lane 7), thyroid carcinoma: SW579 (Lane 8), choriocarcinoma: JAR (Lane 9), glioblastoma: U-87 MG (Lane 10), breast carcinoma: BT-20 (Lane 11), and pancreatic adenocarcinoma: HPAF-2 (Lane 12). The RNA was capillary-transferred to Nytran paper and probed with the $^{32}$P-labeled IA-1-18. Hybridization conditions are provided in Example 4. FIG. 5A illustrates the results obtained from a Northern blot containing total RNA from insulinoma tissues as compared with other transformed cell lines. Human insulinoma tissues and small cell lung carcinoma cells were positive for IA-1 RNA. Results are summarized in Table II. FIG. 1B is a Northern blot of RNA obtained from murine cell lines. Mouse fibroblast: NIH-3T3 RNA was loaded into Lane 1, mouse glucagonoma: alpha TC-1 (Lane 2), mouse insulinoma; beta TC-1 (Lane 3), rat insulinoma: RIN (Lane 4), and hamster insulinoma: HIT (Lane 5). The gel was transferred to Nytran and probed with labelled IA-1-18. A portion of the ethidium bromide stained gel containing the 18S ribosomal RNAs is shown at the bottom of FIG. 5. The cDNA probe strongly cross-hybridized with insulinoma cell lines of mouse, rat and hamster. The mouse glucagonoma cell was faintly positive only after extended exposure times.

EXAMPLE 7

IA-1 Gene Fragments as Probes for Neuroendocrine Tumors

RNA was isolated from human small cell lung cancer biopsies and a variety of human lung cancer cell lines using techniques described in Example 1. Total RNA was separated for Northern analysis using 1% agarose/formaldehyde gel electrophoresis applying techniques described in Example 4. Results indicated that 22 of 22 human small cell lung carcinoma cell lines and 8 of 8 human small cell lung cancer biopsies expressed IA-1 mRNA whereas 15 of 15 non-small cell lung carcinoma cell lines and other human tumor cell lines (as shown in Table II) expressed little of IA-1 associated transcripts. This tissue screening data strongly demonstrated the use of IA-1 and fragments thereof to monitor tumor progression in small cell lung cancer in particular and in neuroendocrine tumors in general.

EXAMPLE 8

Preparation of Antibody to IA-1 Protein

Peptide fragments of fifteen amino acids or greater and substantially purified IA-1 are injected separately into mice in incomplete Freund's adjuvant using techniques well known in the art (Madsen et al., *Endocrinology* 113:2135–2144, 1983 and Beck et al., *Exp. Clin. Endocrinol.* 93:255–260, 1989). Spleens are surgically removed from anesthetized IA-1 sera positive mice and a spleen cell suspension is prepared in Dulbecco's Modified Eagle Medium (DMEM). Splenocytes are minced and fused with log phase Sp2/0 mouse myeloma cells using 50% (vol/vol) polyethylene glycol 1500 in DMEM as described by Madsen et al., supra. Cells are resuspended in HAT medium composed of complete RPMI with $10^{-4}$M hypoxanthine, $4\times10^{-7}$ aminopterin, 1.6×10⁻⁵ M thymidine, and aliquoted at a concentration of 1×10⁵ cells/well into 96-well flat bottom microculture plates (Costar, Cambridge, Mass.) containing 3–4×10⁴ 1-day old feeder cells per well (Contreas et al., Pancreas 5:540–547, 1990).

After 8–16 days, cultures are screened by ELISA for reactivity to IA-1 peptide fragments or protein. ELISA techniques are well known in the art. Following the initial screening with peptide or protein, positive samples are tested on cell lines described in Example 6. Antibody reacting consistently with Northern Blot data from Example 6 is further tested on frozen tissue sections from patients with neuroendocrine tumors using indirect immunofluorescence and/or immunoperoxidase staining, both methods well known in the art. Antibody from positive clones is used to develop kit format diagnostic assays.

Development of immunoassays suitable for diagnostic and research purposes from antibody and antigen is well known in the art. Particular considerations for immunoassay development beyond the scope of this application are detailed in a review by Nakamura et al., 1992. *Immunochemical Assays and Biosensor Technology for the 1990's*. Am. Soc. Microbiol., Wash. D.C.

While particular embodiments of the invention have been described in detail, it will be apparent to those skilled in the art that these embodiments are exemplary rather than limiting, and the true scope of the invention is that defined in the following claims.

We claim:

1. An isolated polynucleotide comprising SEQ ID NO. 1.

2. An isolated polynucleotide encoding a polypeptide having the amino acid sequence of SEQ ID NO. 2.

3. An isolated polynucleotide consisting of the sense or antisense sequence of SEQ NO. 1 or a fragment of at least 10 sequential nucleotides of SEQ ID NO. 1.

4. An isolated polynucleotide consisting of the sense or antisense sequence of SEQ ID NO. 1 or fragment of at least 15 sequential nucleotides of SEQ ID NO. 1.

5. An isolated polynucleotide consisting of the sense or antisense sequence of SEQ ID NO. 1 or a fragment of at least 20 sequential nucleotides of SEQ ID NO. 1.

6. A recombinant expression vector comprising the polynucleotide of claim 3, 4, or 5.

7. Host cells containing the vector of claim 6.

8. An isolated polypeptide comprising SEQ ID NO. 2.

9. An isolated polypeptide consisting of the amino acid sequence of SEQ ID NO. 2 or a fragment of at least 6 sequential amino acids of SEQ ID NO. 2.

10. An isolated polypeptide consisting of the amino acid sequence of SEQ ID NO. 2 or a fragment of at least 10 sequential amino acids of SEQ ID NO. 2.

11. An isolated polypeptide consisting of the amino acid sequence of SEQ ID NO. 2 or a fragment of at least 15 sequential amino acids of SEQ ID NO. 2.

12. Isolated antibodies that specifically bind to a polypeptide having the amino acid sequence of SEQ ID NO. 2.

13. The antibodies of claim 12, wherein said antibodies are monoclonal antibodies.

14. A method of detecting transcription of IA-1 comprising the steps of:

(a) isolating RNA from a biological sample;

(b) contacting said RNA with a polynucleotide that specifically hybridizes with SEQ. ID NO. 1; and (c) detecting hybridization between said polynucleotide and said RNA, wherein said hybridization indicates transcription of IA-1.

15. The method of claim 14, wherein said sample is a tissue section.

16. The method of claim 14, wherein said polynucleotide is labeled for detection.

17. The method of claim 16, wherein said method is a Northern assay.

18. A method of detecting translation of IA-1 comprising the steps of:

(a) obtaining a sample of cells;

(b) contacting said cells with an antibody that specifically binds to a polypeptide having the amino acid sequence of SEQ ID NO. 2; and (c) detecting binding between said antibody and said cells, wherein said binding indicates translation of IA-1.

19. The method of claim 18, wherein said method is an Enzyme-linked Immunosorbant assay.

20. The method of claim 18, wherein said method is a Western Blot assay.

21. The method of claim 18, wherein said sample is a tissue section.

22. An isolated polynucleotide IA-1-34, defined as having a sequence extending 1508 bp upstream from the 3' end of the poly(A) tail of SEQ ID NO. 1.

23. An isolated polynucleotide IA-1-18, defined as having a sequence from bp position 4 to 2819 of SEQ ID NO.1.

* * * * *